(12) United States Patent
Rickard

(10) Patent No.: US 9,339,187 B2
(45) Date of Patent: May 17, 2016

(54) EXTERNAL PRESSURE MEASUREMENT SYSTEM AND METHOD FOR AN INTRAOCULAR IMPLANT

(75) Inventor: Matthew J. A. Rickard, Yorba Linda, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 590 days.

(21) Appl. No.: 13/408,507

(22) Filed: Feb. 29, 2012

(65) Prior Publication Data

US 2013/0158381 A1 Jun. 20, 2013

Related U.S. Application Data

(60) Provisional application No. 61/576,064, filed on Dec. 15, 2011.

(51) Int. Cl.
*A61B 3/16* (2006.01)
*A61F 9/007* (2006.01)

(52) U.S. Cl.
CPC .............. *A61B 3/16* (2013.01); *A61F 9/00781* (2013.01)

(58) Field of Classification Search
CPC ........... A61B 3/16; A61B 3/165; A61B 3/152
USPC ................................................. 600/398, 399
See application file for complete search history.

(56) References Cited

U.S. PATENT DOCUMENTS

| | | |
|---|---|---|
| 4,089,329 A | 5/1978 | Couvillon et al. |
| 4,206,762 A | 6/1980 | Cosman |
| 4,457,757 A | 7/1984 | Molteno |
| 4,560,375 A | 12/1985 | Schulte et al. |
| 4,604,087 A | 8/1986 | Joseph |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters et al. |

(Continued)

FOREIGN PATENT DOCUMENTS

| | | |
|---|---|---|
| CN | 101360523 | 2/2009 |
| CN | 101466299 | 6/2009 |

(Continued)

OTHER PUBLICATIONS

International Searching Authority, International Search Report, PCT/US2012/66709, Apr. 19, 2013, 4 pages.

(Continued)

*Primary Examiner* — Sean Dougherty
*Assistant Examiner* — Daniel Cerioni

(57) ABSTRACT

An IOP monitoring device for implantation in an eye of a patient may include a first tube having a first opening, the first tube being configured to extend into an anterior chamber of the eye and extend to a first sensor outside the anterior chamber. The first sensor may be in fluid communication with the first opening of the first tube. The device also may include a second tube having an opening spaced from a second sensor. The opening of the second tube may be configured to be exposed to a pressure representative of atmospheric pressure, with the second sensor being in fluid communication with the second opening. In one aspect, a patch is attachable to a globe of the eye and configured to lie over the opening of the second tube and secure the opening in place in the eye.

13 Claims, 2 Drawing Sheets

(56) References Cited

U.S. PATENT DOCUMENTS

| | | |
|---|---|---|
| 5,005,577 A | 4/1991 | Frenkel |
| 5,083,742 A | 1/1992 | Wylie et al. |
| 5,178,604 A | 1/1993 | Baerveldt |
| 5,179,953 A | 1/1993 | Kursar |
| 5,397,300 A | 3/1995 | Baerveldt |
| 5,433,701 A | 7/1995 | Rubinstein |
| 5,466,233 A | 11/1995 | Weiner et al. |
| 5,476,445 A | 12/1995 | Baerveldt |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,702,618 A | 12/1997 | Saaski et al. |
| 5,707,643 A | 1/1998 | Ogura et al. |
| 5,722,948 A | 3/1998 | Gross |
| 5,891,097 A | 4/1999 | Saito |
| 5,910,110 A | 6/1999 | Bastable |
| 6,007,511 A | 12/1999 | Prywes |
| 6,048,328 A | 4/2000 | Haller et al. |
| 6,050,970 A | 4/2000 | Baerveldt |
| 6,251,090 B1 | 6/2001 | Avery et al. |
| 6,261,256 B1 | 7/2001 | Ahmed |
| 6,443,893 B1 | 9/2002 | Schnakenberg et al. |
| 6,447,449 B1 | 9/2002 | Fleischman et al. |
| 6,468,283 B1 | 10/2002 | Richter et al. |
| 6,533,733 B1 | 3/2003 | Ericson et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,726,676 B2 | 4/2004 | Stegmann et al. |
| 6,749,568 B2 | 6/2004 | Fleischman et al. |
| 6,939,299 B1 | 9/2005 | Petersen et al. |
| 6,962,573 B1 | 11/2005 | Wilcox |
| 6,976,982 B2 | 12/2005 | Santini, Jr. et al. |
| 7,025,740 B2 | 4/2006 | Ahmed |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,304,334 B2 | 12/2007 | Agarwal et al. |
| 7,354,416 B2 | 4/2008 | Quiroz-Mercado et al. |
| 7,409,863 B2 | 8/2008 | Bateman et al. |
| 7,544,176 B2 | 6/2009 | Rodgers et al. |
| 7,612,328 B2 | 11/2009 | Kaiser |
| 7,648,465 B2 | 1/2010 | Gordon |
| 7,756,559 B2 | 7/2010 | Abreu |
| 7,824,699 B2 | 11/2010 | Ralph et al. |
| 8,123,687 B2 | 2/2012 | Dacquay et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 8,545,431 B2 | 10/2013 | Rickard |
| 8,549,925 B2 | 10/2013 | Tai et al. |
| 8,579,848 B2 | 11/2013 | Field et al. |
| 8,585,631 B2 | 11/2013 | Dacquay |
| 8,814,820 B2 | 8/2014 | Bergheim et al. |
| 8,840,578 B2 | 9/2014 | Dos Santos et al. |
| 2001/0000527 A1 | 4/2001 | Yaron et al. |
| 2002/0013546 A1 | 1/2002 | Grieshaber et al. |
| 2002/0019607 A1 | 2/2002 | Bui |
| 2002/0049374 A1 | 4/2002 | Abrea |
| 2002/0087111 A1 | 7/2002 | Ethier et al. |
| 2002/0099359 A1 | 7/2002 | Santini, Jr. et al. |
| 2002/0103412 A1 | 8/2002 | Trimmer |
| 2002/0139947 A1 | 10/2002 | Wang |
| 2002/0143284 A1 | 10/2002 | Tu et al. |
| 2002/0156461 A1 | 10/2002 | Joshi |
| 2002/0175191 A1 | 11/2002 | Joshi |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado |
| 2005/0016866 A1 | 1/2005 | Kramer |
| 2005/0049578 A1 | 3/2005 | Tu et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0041220 A1 | 2/2006 | Boukhny et al. |
| 2006/0131350 A1 | 6/2006 | Schechter et al. |
| 2006/0189916 A1 * | 8/2006 | Bas .................................. 604/8 |
| 2007/0019156 A1 | 1/2007 | Fink |
| 2007/0032757 A1 | 2/2007 | Medow |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischmann et al. |
| 2007/0156079 A1 | 7/2007 | Brown |
| 2007/0212397 A1 | 9/2007 | Roth |
| 2007/0255262 A1 | 11/2007 | Haase |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2008/0257915 A1 | 10/2008 | Wold |
| 2009/0069648 A1 | 3/2009 | Irazqui et al. |
| 2009/0076367 A1 | 3/2009 | Sit et al. |
| 2009/0143713 A1 | 6/2009 | Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0114006 A1 | 5/2010 | Baerveldt |
| 2010/0121248 A1 | 5/2010 | Yu et al. |
| 2010/0121348 A1 | 5/2010 | Van Der Burg et al. |
| 2010/0174272 A1 | 7/2010 | Weiner |
| 2010/0222769 A1 | 9/2010 | Meng et al. |
| 2010/0222770 A1 | 9/2010 | Gordon |
| 2010/0234717 A1 | 9/2010 | Wismer |
| 2010/0253167 A1 | 10/2010 | Charnley et al. |
| 2010/0280349 A1 | 11/2010 | Dacquay et al. |
| 2010/0305550 A1 | 12/2010 | Meng et al. |
| 2011/0046536 A1 | 2/2011 | Stegman et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0077626 A1 | 3/2011 | Baerveldt et al. |
| 2011/0248671 A1 | 10/2011 | Dos Santos et al. |
| 2012/0004528 A1 | 1/2012 | Li et al. |
| 2012/0022505 A1 | 1/2012 | Dacquay et al. |
| 2012/0022506 A1 | 1/2012 | Rickard et al. |
| 2012/0296258 A1 | 11/2012 | Rickard et al. |
| 2013/0085440 A1 | 4/2013 | Bohm et al. |
| 2013/0144202 A1 | 6/2013 | Field et al. |
| 2013/0150775 A1 | 6/2013 | Dos Santos et al. |
| 2013/0150777 A1 | 6/2013 | Bohm et al. |
| 2013/0204177 A1 | 8/2013 | Field et al. |
| 2013/0218064 A1 | 8/2013 | Rickard |
| 2013/0338564 A1 | 12/2013 | Rickard et al. |
| 2014/0039374 A1 | 2/2014 | Dos Santos et al. |

FOREIGN PATENT DOCUMENTS

| | | |
|---|---|---|
| DE | 4438201 | 5/1996 |
| EP | 0102747 A1 | 3/1984 |

(56) References Cited

FOREIGN PATENT DOCUMENTS

| | | | |
|---|---|---|---|
| EP | 1195523 | A2 | 4/2002 |
| EP | 1917987 | A2 | 5/2008 |
| JP | 03049775 | | 3/1991 |
| WO | 9303665 | A1 | 3/1993 |
| WO | 9803665 | A1 | 1/1998 |
| WO | 9803809 | A1 | 1/1998 |
| WO | 9938470 | A2 | 8/1999 |
| WO | 9938470 | A3 | 10/1999 |
| WO | 0174427 | A1 | 10/2001 |
| WO | 0194784 | A1 | 12/2001 |
| WO | 02056758 | A1 | 7/2002 |
| WO | 03001991 | A1 | 1/2003 |
| WO | 03102632 | A2 | 12/2003 |
| WO | 2004014218 | A2 | 2/2004 |
| WO | 2005079204 | A2 | 9/2005 |
| WO | 2005088417 | A1 | 9/2005 |
| WO | 2007087061 | A2 | 8/2007 |
| WO | 2007127305 | A2 | 11/2007 |
| WO | 2007136993 | A1 | 11/2007 |
| WO | 2008060649 | A2 | 5/2008 |
| WO | 2008061043 | A2 | 5/2008 |
| WO | 2008084350 | A2 | 7/2008 |
| WO | 2008094672 | A2 | 8/2008 |
| WO | 2008084350 | A3 | 10/2008 |
| WO | 2008094672 | A3 | 11/2008 |
| WO | 2009010799 | A2 | 1/2009 |
| WO | 2009026499 | A1 | 2/2009 |
| WO | 2009049686 | A1 | 4/2009 |
| WO | 2009081031 | A2 | 7/2009 |
| WO | 2010129446 | A1 | 11/2010 |
| WO | 2010136071 | A1 | 12/2010 |
| WO | 2011034727 | A1 | 3/2011 |
| WO | 2011034738 | A1 | 3/2011 |
| WO | 2011034740 | A1 | 3/2011 |
| WO | 2011034742 | A2 | 3/2011 |
| WO | 2011035218 | A1 | 3/2011 |
| WO | 2011034742 | A3 | 5/2011 |
| WO | 2012012017 | A1 | 1/2012 |
| WO | 2013052332 | A1 | 4/2013 |
| WO | 2013058943 | A1 | 4/2013 |
| WO | 2013085894 | A2 | 6/2013 |
| WO | 2013085895 | A1 | 6/2013 |
| WO | 2013090006 | A1 | 6/2013 |
| WO | 2013090231 | A1 | 6/2013 |
| WO | 2013123142 | A1 | 8/2013 |

OTHER PUBLICATIONS

International Searching Authority, Written Opinion of the International Searching Authority, PCT/ US2012/66709, Apr. 19, 2013, 5 pages.
Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Implant"; Journal of Micromechanics and Microengineering, 13 (2003); pp. 613-619.
Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.
Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
International Searching Authority, International Search Report, PCT/ US2010/033329, Jul. 13, 2010, 4 pages.
International Searching Authority, Search Report and Written Opinion of the International Searching Authority, PCT/US2010/033329, Jul. 13, 2010, 8 pages.
International Searching Authority, International Search Report, PCT/ US2010/047429, Nov. 1, 2010, 15 pages.
International Searching Authority, Written Opinion of the International Searching Authority, PCT/ US2010/047429, Nov. 1, 2010, 8 pages.
International Searching Authority, International Search Report, PCT/ US2010/047600, Dec. 14, 2010, 5 pages.
International Searching Authority, Written Opinion of the International Searching Authority, PCT/ US2010/047600, Dec. 14, 2010, 7 pages.
International Searching Authority, International Search Report, PCT/ US2010/049424, Nov. 26, 2010, 6 pages.
International Searching Authority, Written Opinion of the International Searching Authority, PCT/ US2010/049424, Nov. 26, 2010, 8 pages.
International Searching Authority, International Search Report, PCT/ US2011/036742, Aug. 17, 2011, 2 pages.
International Searching Authority, Written Opinion of the International Searching Authority, PCT/ US2011/036742, Aug. 17, 2011, 5 pages.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded For Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer For Direct Intraocular Pressure Measurements," 1st European Conference on Biomedical Engineering, Feb. 1991, pp. 194-195, vol. 17, No. 20, Nice, France.
Walter, Peter; Intraocular Pressure Sensor: Where Are We—Where Will We Go? Journal Graefe's Archive For Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati M.D., et al.; "Mini Drug Pump for Ophthalmic Use"; Trans Am Ophthalmol Soc 2009; 107; pp. 60-71.
Stemme et al.; "A Valveless Diffuser/Nozzle-Based Fluid Pump"; ScienceDirect; Sensors and Actuators A, 39; pp. 159-167 (1993).
Nisar, et al.; MEMS-Based Micropumps in Drug Delivery and Biomedical Applications; ScienceDirect; Sensors and Actuators B 130; pp. 917-942 (2008).
International Searching Authority, International Search Report, PCT US2010/047605; Dec. 16, 2010, 7 pages.

(56) References Cited

OTHER PUBLICATIONS

International Searching Authority, Written Opinion of the International Searching Authority, PCT US2010/047605; Dec. 16, 2010, 9 pages.
Internationl Searching Authority, International Search Report, PCT/US2010/047612; Dec. 21, 2010, 7 pages.
Internationl Searching Authority, Written Opinion of the International Searching Authority, PCT/ US2010/047612; Dec. 21, 2010, 10 pages.
Driot et al.; "Ocular pharmacokinetics of fluocinolone acetonide after RetisertTM intravitreal implantation in rabbits over a 1-year period"; J. Ocular Pharm; 20; 3;pp. 269-275.
Glybina et al.; "Neuroprotective properties of fluocinolone acetonide chronically delivered into the vitreous of albino RCS rats"; IVOS; 47; ARVO e-Abstract 1028.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Miyamoto H et al., 1997, Biodegradable scleral implant for intravitreal controlled release of fluconazole, Curr Eye Res, 16(9), 930-935.
Mruthyunjaya P et al., 2003, "An intravitreal sustained release fluocinolone acetonide device to treat severe experimental uveitis", IOVS, 44, ARVO E-Abs 4215.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
See R F et al., 2006, "Safety and drug release profile of injectable intravitreal sustained-release fluocinolone acetonide device", IOVS, 47, ARVO E-Abs 5119.
Tano R et al., 2005, Helical intravitreal implant: surgical method development and outcomes, IOVS, 46, ARVO E-Abs 483.
Varner S E et al., 2003, "Development of a minimally invasive intravitreal implant for drug delivery", IOVS, 44, ARVO E-Abs 4214.
Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.
Yasukawa T et al., 2001, "Biodegradable scleral plugs for vitreoretinal drug delivery", Adv. Drug Del Rev., 52(1), 25-36.
International Searching Authority, International Search Report, PCT/US2013/026066, Apr. 17, 2013, 5 pages.
International Searching Authority, Written Opinion of the International Searching Authority, PCT/ US2013/026066, Apr. 17, 2013, 8 pages.
Dacquay, Bruno, Intraocular Pressure Sensor, Prosecution History, U.S. Appl. No. 12/434,709, filed May 4, 2009, 566 pages.
Rickard, Matthew J.A., Lumen Clearing Valve for Glaucoma Drainage Device, Prosecution History, U.S. Appl. No. 12/609,043, filed Oct. 30, 2009, 1507 pages.
Rickard, Matthew, Intraocular Pressure Sensor with External Pressure Compensation, Prosecution History, U.S. Appl. No. 12/563,244, filed Sep. 21, 2009, 562 pages.
Dos Santos, Cesario, Power Generator for Glaucoma Drainage Device, Prosecution History, U.S. Appl. No. 12/685,772, filed Jan. 12, 2010, 517 pages.
Dacquay, Bruno, Closed Loop Glaucoma Drug Delivery System, Prosecution History, U.S. Appl. No. 13/109,155, filed May 17, 2011, 238 pages.
Field, Leslie, Active Drainage Systems with Pressure-Driven Valves and Electronically-Driven Pump, Prosecution History, U.S. Appl. No. 13/315,329, filed Dec. 9, 2011, 1620 pages.
Rickard, Matthew J.A., Power Saving Glaucoma Drainage Device, Prosecution History, U.S. Appl. No. 12/837,803, filed Jul. 16, 2010, 1725 pages.
Dos Santos, Cecario P., Multilayer Membrane Actuators, Prosecution History, U.S. Appl. No. 13/315,905, filed Dec. 9, 2011, 1652 pages.
Parkhutik, Vitali, et al., The Role of Hydrogen in the Formation of Porous Structures in Silicon, Materials Science & Engineering, 1999, B58, 95-99, Elsevier Science, S.A.
Rickard, Matthew, Intraocular Pressure Sensor with External Pressure Compensation, Prosecution History, U.S. Appl. No. 14/267,443, filed May 1, 2014, 53 pages.
Rickard, Matthew, Intraocular Pressure Sensor with External Pressure Compensation, Prosecution History, U.S. Appl. No. 13/565,907, filed Aug. 3, 2012, 1652 pages.
Barton, Keith, et al., "The Ahmed Baerveldt Comparison Study," Journal of Ophthalmology, received Feb. 5, 2010, available online Oct. 8, 2010, vol. 118, No. 3, Elsevier, Inc., USA, pp. 435-442.
International Searching Authority, International Preliminary Report on Patentability, PCT/US2012/057261, Apr. 25, 2013, 10 pages.
International Searching Authority, Written Opinion of the International Searching Authority, PCT/2012/057261, Apr. 18, 2014, 10 pages.
Rickard, Matthew, Intraocular Pressure Sensor with External Pressure Compensation, Prosecution History, U.S. Appl. No. 14/267,443, filed May 1, 2014, 2153 pages. (2 pdf files).

* cited by examiner

EXTERNAL PRESSURE MEASUREMENT SYSTEM AND METHOD FOR AN INTRAOCULAR IMPLANT

PRIORITY CLAIM

This application claims the benefit of priority of U.S. Provisional Patent Application Ser. No. 61/576,064 titled "EXTERNAL PRESSURE MEASUREMENT SYSTEM AND METHOD FOR AN INTRAOCULAR IMPLANT", filed on Dec. 15, 2011, whose inventor is Matthew J. A. Rickard, which is hereby incorporated by reference in its entirety as though fully and completely set forth herein.

BACKGROUND

The present disclosure relates generally to an external pressure measurement system for use in ophthalmic treatments. In some instances, embodiments of the present disclosure are configured to be part of an intraocular implant comprising an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases over time. This development and progression of fibrosis reduces or eliminates flow from the anterior chamber, reducing the capacity of the drainage device to affect IOP.

The system and methods disclosed herein overcome one or more of the deficiencies of the prior art.

SUMMARY

In one exemplary aspect, the present disclosure is directed to an IOP monitoring device for implantation in an eye of a patient. The device includes a first tube having a first opening, the first tube being configured to extend into an anterior chamber of the eye and extend to a first sensor outside the anterior chamber, the first sensor in fluid communication with the first opening of the first tube. The device also includes an atmospheric sensing subsystem configured to be exposed to a pressure representative of atmospheric pressure, the atmospheric sensing subsystem comprising a second sensor. In one aspect, the atmospheric sensing subsystem includes a second tube having an opening spaced from the second sensor, the opening of the second tube being configured to be exposed to a pressure representative of atmospheric pressure, the second sensor being in fluid communication with the second opening.

In another exemplary aspect, the present disclosure is directed to an IOP monitoring device for implantation in an eye of a patient. The device includes a main portion configured to be implanted in a subconjunctival pocket, and a first tube extending from the main portion and having a length selected to extend from the main portion in the subconjunctival pocket to an anterior chamber of the eye. The first tube may have a first open end disposable in the anterior chamber. The device also includes a second tube extending from the main portion, with the second tube having an open end. A pressure sensor may be associated with the second tube to detect a pressure at a location spaced apart from the main portion. A patch may be disposed over the opening of the second tube.

In another exemplary aspect, the present disclosure is directed to a method of treating an ocular condition. The method may include implanting an IOP monitoring device in an ocular space including disposing a first opening of a first tube in an anterior chamber, and arranging a first opening of a second tube at a location outside the anterior chamber. The method also may include detecting a first pressure within the first tube, where the first pressure is representative of the anterior chamber pressure, and detecting a second pressure within the second tube, where the second pressure is representative of atmospheric pressure. In one aspect, the method includes draining aqueous humor from within the anterior chamber through the first tube to a drainage site outside the anterior chamber. In one aspect, the method includes implanting a patch over the second opening of the second tube to secure the second tube in a manner reducing wear on adjacent tissue.

In another exemplary aspect, the present disclosure is directed to IOP monitoring device for implantation in an eye of a patient that includes a main portion configured to be implanted in a subconjunctival pocket, and includes a drainage tube extending from the main portion and having a length selected to extend from the main portion in the subconjunctival pocket to an anterior chamber of the eye. The drainage tube may have an open end disposable in the anterior chamber and configured to drain aqueous humor from the anterior chamber to a drainage site outside the anterior chamber. A pressure sensor is disposed on the drainage tube at a location spaced from the open end and spaced apart from the main portion, and a patch is disposable over the pressure sensor.

In another exemplary aspect, the present disclosure is directed to a method of treating an ocular condition that includes implanting an IOP monitoring device in an ocular space including disposing a first opening of a first tube of an implant in an anterior chamber and including disposing a body portion of the implant in a subconjunctival pocket. A first pressure may be detected within the first tube, with the first pressure being representative of the anterior chamber pressure. A second pressure representative of atmospheric pressure may be detected with the IOP monitoring device at a location outside the pericardium and outside the anterior chamber.

In another exemplary aspect, the present disclosure is directed to an IOP monitoring device that includes a first tube having a first opening configured to be disposed in an anterior chamber of the eye and subject to anterior chamber pressure, and includes a second tube having a second opening configured to be disposed at location outside the anterior chamber of the eye in an area subject to a pressure representative of atmospheric pressure. A main body is in communication with the first and second tubes. The main body includes a pressure element responsive to the anterior chamber pressure and the pressure representative of atmospheric pressure. In one aspect, the pressure element is one of a membrane valve and at least one pressure sensor. In one aspect, the device further includes a patch disposed over the second opening.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
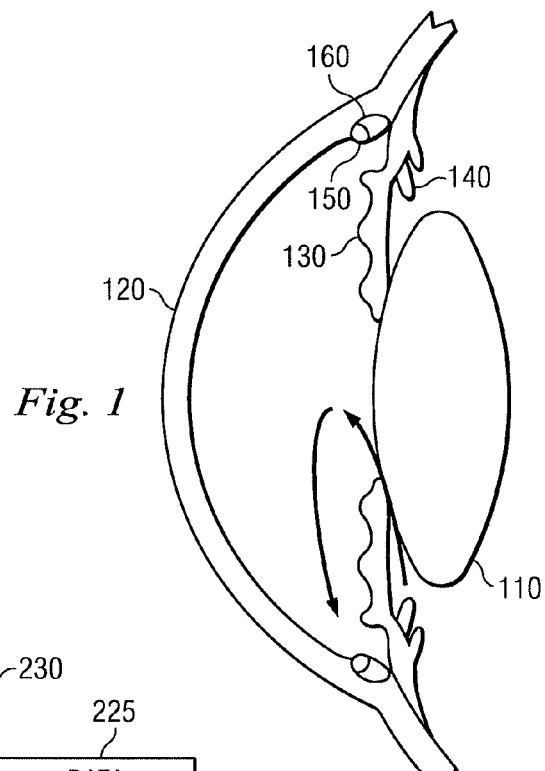
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a method and system for treating an eye disorder by determining the IOP using an atmospheric reference pressure taken at a "dry" subconjunctiva location. A "dry" location, as used herein, is a location spaced apart from an aqueous humor drainage site such that it is not influenced by the wetter tissue at the drainage site. This location may be covered and protected by a biocompatible patch material formed of, for example, donor sclera, pericardium, or others. Since atmospheric pressure is a factor used to determine IOP, the accuracy of the IOP measurement corresponds to the accuracy of the atmospheric pressure reading. Therefore, it is important that the system relatively accurately indicate the atmospheric pressure. The systems and methods disclosed herein may enable more accurate IOP determinations resulting in better information for determining treatment, potentially providing more effective treatment and greater customer satisfaction.

Figure 2:
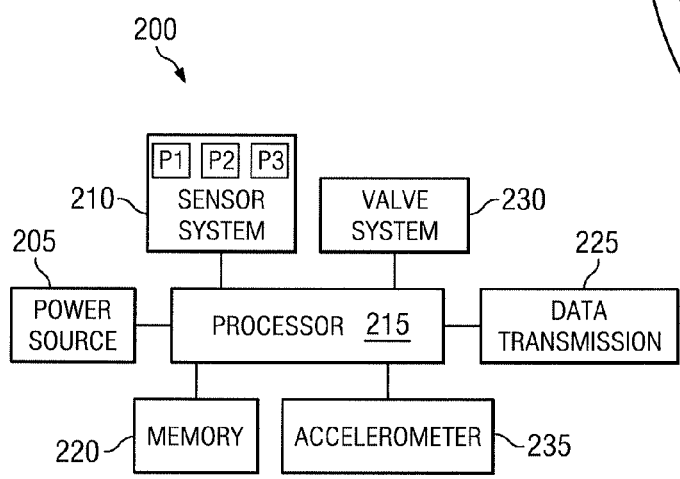
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a data transmission module 225, a valve system 230, and an accelerometer 235. In some embodiments, a gyroscope is used in place of accelerometer 235.

The processor 215 is typically an integrated circuit with power, input, and output pins capable of performing logic functions, or is a controller that controls different components that perform different functions. The memory 220 may be a semiconductor memory that interfaces with the processor 215. In one example, the processor 215 can write to and read from the memory 220. For example, the processor 215 can be configured to read data from the sensor system 210 and write that data to the memory 220. In this manner, a series of sensed or calculated IOP readings can be stored in the memory 220. The processor 215 is also capable of performing other basic memory functions, such as erasing or overwriting the memory 220, detecting when the memory 220 is full, and other common functions associated with managing semiconductor memory.

The valve system 230 may be a passive valve, a pressure driven valve, an electronically controlled valve or other type of valve and may affect flow of aqueous humor through the IOP control system 200. It may include any number of valves and valve types in combination. Some embodiments also include one or more pumping systems that cooperate with one or more valves to provide pressure relief when needed. The valve system 230 may operate under the control of the processor 215 and may receive instructions from the processor to permit increased flow of aqueous humor from the anterior chamber or to decrease flow to meet a desired flow rate and pressure. In one embodiment, the valve system 230 comprises a pressure-driven valve having a pressure element, such as membrane, actuated by pressure differentials. In such valves, pressure in the anterior chamber provides a biasing force on one side of the membrane while pressure at a separate location provides an opposing biasing force on the other side of the membrane. In one example, the pressure at the separate location may be atmospheric pressure or a pressure based on atmospheric pressure. Pumps are also contemplated and may form a part of the valve system or a separate part of the IOP control system 200.

As shown in FIG. 2, the exemplary IOP sensor system 210 includes at least three pressure elements as pressure sensors P1, P2, and P3. These pressure sensors can be any type of pressure sensors suitable for implantation in the eye. They each may be the same type of pressure sensor, or they may be different types of pressure sensors.

Generally, IOP is a gauge pressure reading—the difference between the absolute pressure in the eye (as measured by the sensor P1) and atmospheric pressure (as measured by the sensor P3). Atmospheric pressure, typically about 760 mm Hg (millimeters (mm) of mercury), often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Thus, for accurate monitoring of IOP, it is desirable to have pressure readings for the anterior chamber (as measured by the sensor P1) and atmospheric pressure in the vicinity of the eye (as measured by the sensor P3).

Therefore, in one embodiment of the present disclosure, pressure readings are taken by the pressure sensors P1 and P3 simultaneously or nearly simultaneously over time so that the actual IOP can be calculated (as P1−P3 or P1−f(P3), where f(P3) indicates a function of P3). The processor 215 may perform any calculations based on the data obtained by the sensors P1, P2, and P3. The pressure readings of sensors P1 and P3 and the results of any calculations can be stored in the memory 220 by the processor 215. They can later be read from memory so that actual IOP over time can be interpreted by a physician.

Readings from the pressure sensors P1, P2, and P3 can be used to control the flow rate through the valve system 230. For example, the valve system 230 may be controlled based on the pressure readings from pressure sensors P1, P2, and P3. That is, the valve system 230 may be controlled by the microprocessor 215 based on input data received from the sensors. A desired pressure differential (that corresponds to a desired flow rate) can be maintained by controlling the operation of the valve system 230. Likewise, various intraocular pressure parameters, such as, by way of non-limiting example, a desired IOP, an IOP change rate, and/or a bleb pressure may be controlled by controlling the operation of valve system 230.

In some embodiments, the IOP control system 200 also includes an accelerometer 235 that communicates with the processor 215 and may provide information relating to the particular orientation of the IOP control system 200. As will become more apparent below, this may permit the processor to recognize variations in sensor data that may occur as a result of a patient's physical position (e.g., upright, prone, etc.). In some situations, this could enable more accurate analysis of pressures by recognizing when pressure variations result from patient orientation rather than other conditions. The accelerometer 235 is described further below.

Figure 3:
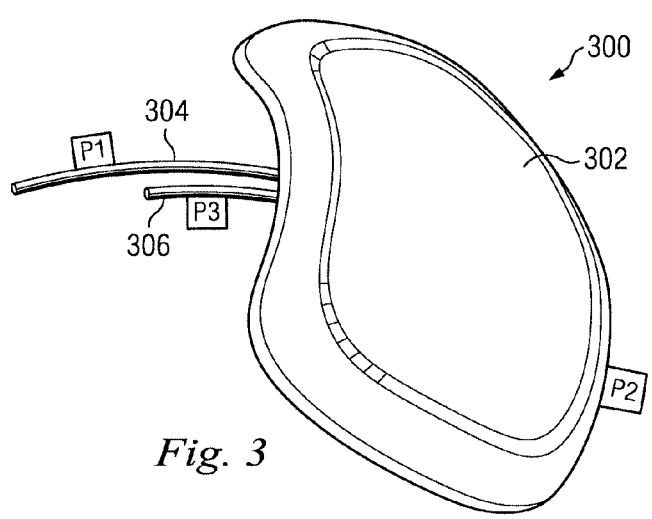
FIG. 3 is a schematic diagram of an ocular implant that carries the IOP control system of FIG. 2 according to an exemplary aspect of the present disclosure.

FIG. 3 is a diagram of an exemplary IOP monitoring device shown as an ocular implant or drainage device 300 that carries the IOP control system 200. The drainage device 300 includes a plate 302, a drainage tube 304, and an atmospheric pressure tube 306. A patch, described with reference to FIGS. 4 and 5 below, may also form a part of the drainage device 300. The plate 302 is arranged to carry various components of the IOP control system 200 that are shown in FIG. 2. For example, it may include the power source 205, elements of the IOP sensor system 210, the processor 215, the memory 220, the data transmission module 225, the valve system 230, and the accelerometer 235. It may also carry sensors of the sensor system 210.

The plate 302 is configured to fit at least partially within the subconjunctival space and is sized for example within a range between about 15 mm×12 mm to about 30 mm×15 mm and has a thickness less than about 2 mm thick and preferably less than about 1 mm thick. The plate 302 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

The drainage tube 304 extends from an anterior side of the plate 302 and is sized and arranged to extend into the anterior chamber of the eye. The drainage tube 304 includes an open end and a lumen that extends to a second open end disposed at a drainage site. The second open end may be formed in the plate 302, so long as aqueous humor can flow from the anterior chamber to the drainage site. The drainage site may be approximately the location of the plate. The atmospheric pressure tube 306 also extends from an anterior side of the plate 302. As described in greater detail below, the atmospheric pressure tube 306 provides access to a location having a pressure representative of atmospheric pressure. It is spaced apart from the plate 302 and from tissue that may become pressurized from drainage or that may be affected by formation of a bleb that may affect the natural tissue pressures. Accordingly, in this example, the atmospheric pressure tube 306 has a length sufficient to remove it from areas that may potentially be affected by the drainage or blebs that may form at the drainage site (see further discussion below relating to scenarios in which the accelerometer 235 is or is not required). Here, the atmospheric pressure tube 306 runs substantially parallel to or in the same longitudinal direction as the drainage tube 304. However, since it is not intended to reach the anterior chamber, the atmospheric pressure tube 306 is shorter than the drainage tube 304. As indicated above, it includes an open end that is exposed to atmospheric pressure or to pressures indicative of atmospheric pressure. In some embodiments, the exterior surfaces of tube 306 and tube 304 are physically attached, thus providing little or no change to the surgical procedure for implantation of tube/plate glaucoma drainage devices. That is, this compactness can provide essentially no required modification to a surgeon's current procedure.

As represented in FIG. 3, the pressure sensor P1 is located in or is in fluidic communication with the anterior chamber 340, the pressure sensor P2 is located at or is in fluidic communication with a drainage site, and the pressure sensor P3 is located at or is in communication with the opening in the atmospheric pressure tube 306 in a manner to measure atmospheric pressure or collect measurements indicative of atmospheric pressure. In some embodiments, the pressure sensor P1 is located within or is in fluid communication with the lumen of the drainage tube 304 which is in fluid communication with the anterior chamber. Likewise, in some embodiments, the pressure sensor P3 is located within or is in fluid communication with the lumen of the atmospheric pressure tube 306. In some embodiments, sensors P1, P2, and P3 reside on the plate, such as plate 302, along with some or all components of IOP control system 200.

In some embodiments, the drainage tube 304 drains aqueous humor from the anterior chamber 340 of the eye. The valve system 230 controls the flow of aqueous humor through the tube 304. In the embodiment shown, the pressure sensor P1 measures the pressure in the tube 304 upstream from the valve system 230 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In other embodiments, flow is not realized through tube 304 and thus tube 304 serves primarily as a means for fluidic communication between the anterior chamber and a modified version of the IOP control system 200, which operates with the valve system 230 being inactive or not physically present at all. Though such embodiments do not control IOP, such systems still provide a clinical benefit by providing real-time, continuous, IOP monitoring since pressure sensed via sensor P1 can still be monitored (in fact, it is slightly more accurate in comparison to the case of tube 304 serving to drain fluid). Pressure sensed via sensor P3 is obtained in the same manner as the drainage (flowing) version. Pressure sensed via sensor P2 in this version serves as a secondary source of a reference pressure equivalent to or correlating with atmospheric pressure. Such as system may be advantageous for a patient not necessarily needing immediate IOP relief but is a prospect for needing drainage IOP relief later in time and, that would benefit from continuous, accurate, logged IOP monitoring. Such a system would be further merited if the patient is already undergoing a non-related surgery, such as cataract surgery. The described use may also be realized when a previously functioning device fails to provide adequate aqueous flow throughput, possibly due to excessive fibrosis at the drainage site, yet may still function properly as an IOP monitoring device.

Returning to FIG. 3, the drainage tube 304 shunts fluid to a drainage location, which may be at any of numerous locations within the eye. For example, some drainage tubes are arranged to shunt aqueous humor from the anterior chamber 340 to the subconjunctival space, thus forming a bleb under the conjunctiva or alternatively, to the subscleral space, thus forming a bleb under the sclera. Other drainage tubes shunt aqueous humor from the anterior chamber to the suprachoroidal space, the supraciliary space, the juxta-uveal space, or to the choroid, forming blebs in those respective locations. In other applications, the drainage tube shunts aqueous humor from the anterior chamber to Schlemm's canal, a collector channel in Schlemm's canal, or any of a number of different blood vessels like an episcleral vein. In some examples, the drainage tube even shunts aqueous humor from the anterior chamber to outside the conjunctiva. Each of these different anatomical locations to which aqueous humor is shunted is an example of a drainage location.

The pressure sensor P2 is located at a drainage site. As such, the pressure sensor P2 may be located in or provide pressure indicative of a pocket, such as a bleb, that generally contains aqueous humor or in communication with such a pocket, via a tube for example, and is in a wet location.

In some embodiments of the present disclosure, the atmospheric pressure sensor P3 is in communication with the opening of the atmospheric pressure tube 306, and the opening is disposed in the eye under the conjunctiva. As such, the pressure sensor P3 measures a pressure that can be correlated with atmospheric pressure. For example, true atmospheric pressure can be a function of the pressure reading of the pressure sensor P3. Since its data is collected from a location spaced apart from the plate 302, from the drainage site, and from tissue that may be affected by the drainage site, the pressure sensor P3 may take measurements in a dry or relatively dry portion of the subconjunctival space, potentially providing increased accuracy of atmospheric measurement. Regardless of location, the pressure sensor P3 is intended to measure atmospheric pressure in the vicinity of the eye or at the eye's surface. Because the pressure sensor P3 is in communication with the opening in the tube 306, sensor readings may be isolated from the potentially erroneous influence of the wet tissue or tissue shift that may occur as a result of bleb formation.

In another embodiment, pressure sensor P3 resides directly under the pericardium and although tube 304 is still present in the system, tube 306 is not required. In this embodiment, pressure sensor P3 may be mounted outside of and adjacent to tube 304. In fact, pressure sensor P3 may be physically attached to tube 304 and made very small in size, thus providing little or no change to the surgical procedure for implantation of tube/plate glaucoma drainage devices. That is, this compactness can provide essentially no required modification to a surgeon's current procedure. Electrical power to and signal communication to and from pressure sensor P3 can be achieved either by wireless means or by embedding conductive wire leads within the wall of tube 304.

Working off of the assumption that the clinical relevant pressure is "IOP", where "IOP" is defined as the absolute pressure in the eye (anterior chamber (AC)) less that of the absolute pressure outside the eye, the "IOP" determines the stress (at least) on the cornea. There is not sufficient scientific information in the literature as to whether there is some intermediate pressure (i.e., non-zero gauge pressure) at the outer surface of the sclera. Therefore, for a system designed to determine and monitor "IOP" as defined by current clinical practice (e.g. using a Goldmann tonometer) that is monitoring absolute pressure in anterior chamber and attempting to measure Patm (atmospheric pressure) on the sclera's outer surface, then the system would need to subtract off any pressure above atmospheric realized at the sclera's outer surface (if such a pressure exists). In addition, it is obvious that if the sensor P3 is too close to a suprascleral drainage location, then it will erroneously detect some or all of the gauge (above atmospheric) drainage pressure reading (some of sensor P2's reading) and will thus have error. Therefore, sensor P3—at a minimum—is isolated by some pressure barrier from P2, either one natural in the eye or designed as part of IOP control system 200 or some combination of both. Examples of pressure barriers between sensor P2 and P3 are disclosed in U.S. patent application Ser. No. 12/563,244 (entitled "Intraocular Pressure Sensor with External Pressure Compensation" by Robert Sanchez and Matthew Rickard, filed Sep. 21, 2009), U.S. patent application Ser. No. 12/609,043 (entitled "Glaucoma Drainage Device with Active Valve and Active Lumen-Clearing Mechanism" by Matthew Rickard, filed Oct. 30, 2009), U.S. patent application Ser. No. 12/837,803 (entitled "Power Saving Glaucoma Drainage Device" by Robert Sanchez and Matthew Rickard, filed Jul. 16, 2010), U.S. patent application Ser. No. 13/311,727 (entitled "Bubble-Driven IOP Control System" by Matthew Rickard and Leslie Field, filed Dec. 6, 2011), U.S. patent application Ser. No. 13/251,368 (entitled "Selectable Varied Control Valve Systems for IOP Control Systems" by Leslie Field and Sebastian Bohm, filed Oct. 3, 2011), U.S. patent application Ser. No. 13/316,755 (entitled "Glaucoma Drainage Devices Including Vario-Stable Valves and Associated Systems and Methods" by Matthew Rickard, Leslie Field, and Sebastian Bohm, filed Dec. 12, 2011), and U.S. Provisional Patent Application No. 61/569,608 (entitled "Active Drainage Systems with Dual-Input Pressure Driven Valves" by Matthew Rickard and Leslie Field, filed Dec. 12, 2011), all of which are hereby incorporated by reference in their entirety as though fully and completely set forth herein. Toward this end, part of the spirit of the present invention is to isolate sensor P3 from sensor P2 by employing a tube that provides a means for monitoring sensor P3 outside the vicinity of sensor P2, possibly in the space under the donor pericardium or sclera patch. This concept is supported by a relatively large quantity of tenons expected to reside between the drainage location and the under-pericardium (or under-donor-sclera) space. However, since there is not sufficient scientific information in the literature as to the actual pressure at a location such as this, or any suprascleral location outside the vicinity of the drainage location, two possible system designs are presented. In one, the design of the system assumes this pressure is essentially that of the atmosphere or is consistently some obtainable monotonic function of it. Thus, the sensor P3 behaves just as or very similarly to a sensor P3 disposed outside the body and only a simple additional correction is necessary, if any.

In the second design approach, this location is assumed to be moist and in fluidic communication with liquids in the body. For this case, it can be expected that this fluidic communication would cause a positive gauge pressure (i.e. above atmospheric pressure). In this case, the data obtained by the sensor P3 may be a function of atmospheric pressure, and a calculation may be performed to obtain the atmospheric pressure based on the measured pressure. This is particularly relevant when the patient's physical position may affect the pressure readings obtained by the pressure sensors P1, P2, or P3. For example, the subconjunctival location of the opening of the atmospheric pressure tube 306 may follow atmospheric pressure, but have a "false positive" offset caused by the hydrostatic pressure, where $$P=\rho gh$$

where h is the distance from the subconjunctiva location to the top of the person's head (assuming they are standing or sitting), g is 9.81 m/s² (meters per second squared) and $\rho$ is the density of aqueous humor (almost identical to water). The value of P could be subtracted by the IOP control system 200 with the use of an additional sensor (an accelerometer 235 or gyroscope) and knowing h as a function of the person's gravitational orientation. For example, if the distance from P3 (in the eye) to the top of the patients head, h, is 100 mm, assuming the aqueous humor density is equal to that of water, then P is just above 7 mmHg. Note that P is reduced to less than 0.5 mmHg if the person is lying down, face up wherein h is likely 5 mm or less. It is interesting to note that if the suprascleral location is indeed moist and in fluidic communication with liquids in the body, then IOP might need to be redefined wherein one aims to define a pressure that describes the overall stress on the cornea and sclera and thus takes into account this superscleral pressure, possibly by averaging or integrating it over the eye's surface area (along with the supracorneal zero gauge pressure) and weighting such a mathematical expression based on surface area fraction, thereby providing some modified "IOP" metric. Pressure would correspondingly increase substantially if the patient were hanging upside down.

To accomplish the offset calculation described above, and provide a more accurate pressure reading regardless of the physical orientation of the patient, the IOP control system 200 may have stored therein some physical dimensions of the patient. For example, the IOP control system 200 may include values stored therein including one or more of, for example, the distance from the center of the eye to the top of the patient's head, the distance from the center of the eye to the bottom of the patient's feet, the distance from the back of the patient's head to the center of patient's eye, among others. These values may be input by the surgeon into the memory 220 of the IOP control system 200 and stored and accessed to calculate the IOP.

Figure 4:
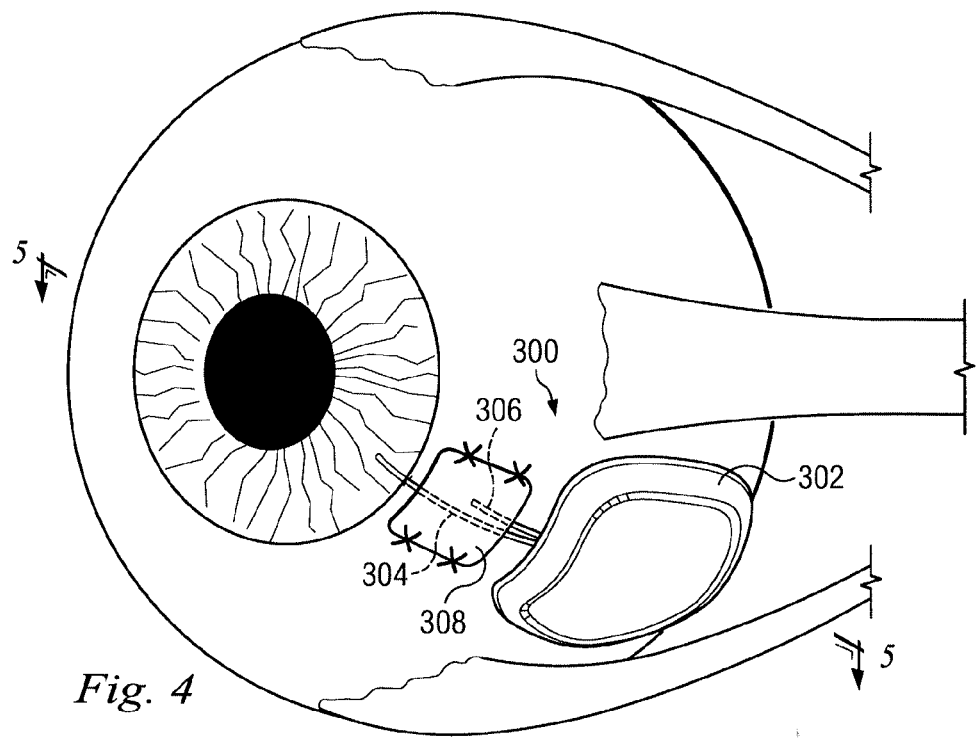
FIG. 4 is a schematic diagram of an exemplary ocular implant in place on an eye according to an exemplary aspect of the present disclosure.
Figure 5:
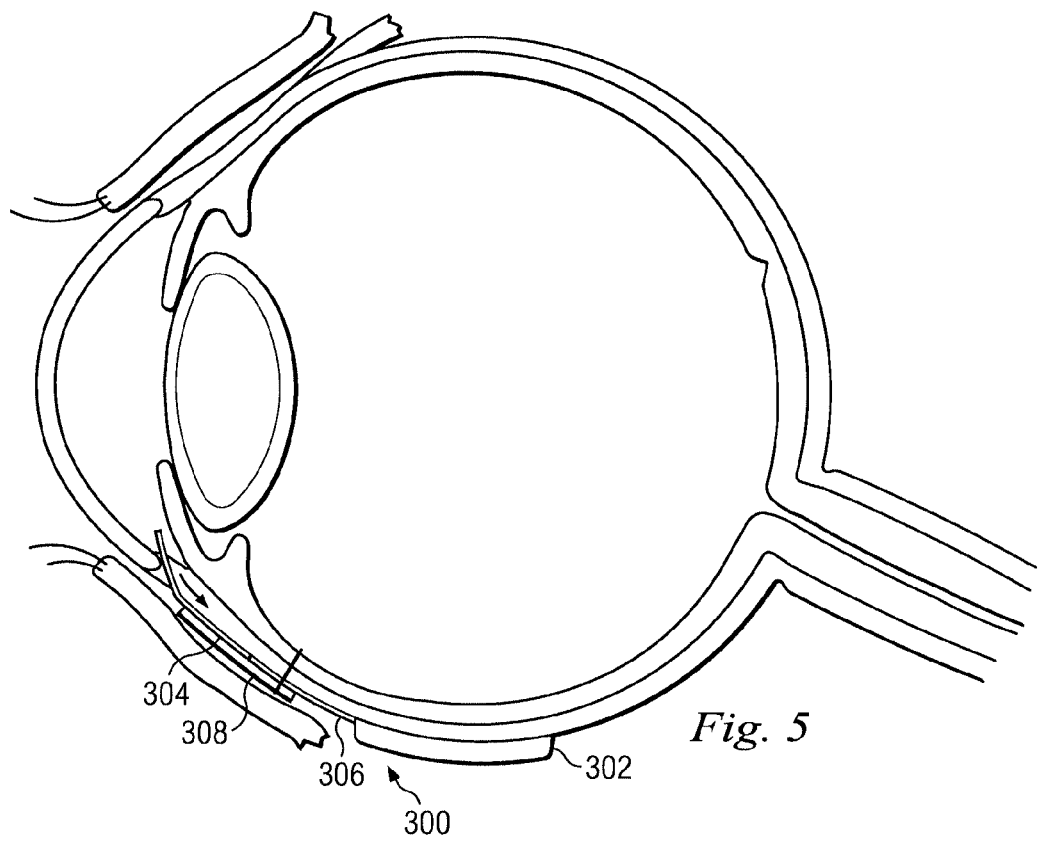
FIG. 5 is a schematic diagram of a cross-sectional view of the exemplary ocular implant of FIG. 4 according to an exemplary aspect of the present disclosure.

FIGS. 4 and 5 are diagrams of one possible application of the ocular implant or drainage device 300 in the eye. FIG. 4 shows the drainage device 300 disposed on the globe of the eye and FIG. 5 shows one example of a cross-sectional view of the eye, taken partially through the drainage device 300. In addition, FIGS. 4 and 5 show a patch 308 that may be used to cover the open end of the atmospheric pressure tube 306 and may be used to hold the drainage tube 304 in place to prevent inadvertent displacement. Patch 308 may also be used to cover a portion of drainage tube 304, as is commonly done is glaucoma tube surgery. Referring to these figures, the plate 302 is located in the subconjunctival pocket between the conjunctiva and sclera. The plate is generally located on an ocular quadrant commonly used for conventional glaucoma drainage devices with plates; that is, it is centered such that it is equidistance from the neighboring ocular muscles that define that the ocular quadrant chosen for implantation, as shown in FIG. 4. The drainage tube 304 bridges the anterior chamber and the plate 302 in the subconjunctival pocket to provide an auxiliary flow path for aqueous humor, bypassing the flow-resistive conventional pathway through the trabecular meshwork and shunting aqueous humor directly to a drainage site.

In one embodiment, the atmospheric pressure tube 306 permits atmospheric pressure to be monitored or approximated at a location spaced from the plate 302 at a relatively "dry" location in the subconjunctiva. Here, the opening to the atmospheric pressure tube 306 is disposed at a location anterior of the plate 302 at the dry location in the subconjunctiva.

In this example, the dry location is also covered by the patch 308. The patch may be formed of any suitable, biocompatible material, and some embodiments may comprise preserved donor sclera or pericardium. As can be seen in both FIGS. 4 and 5, the drainage tube 302 is also covered with the patch 308. The patch 308 protects the conjunctiva by ensuring that the portion of tubing between the plate 308 and the anterior chamber is not in direct contact with the conjunctiva post operatively, which could cause erosion and eventually expose one or both of the tubes 304, 306. As best seen in FIG. 4, the patch 308, whether made of the donor sclera, pericardium, or other material, is sutured in place and then the conjunctiva is closed.

The atmospheric pressure tube 306 resides along side the drainage tube 304, with one end of the atmospheric pressure tube 306 connected to the plate 302 and the other end terminating under the patch 308. This space under the patch is at (or approximates) atmospheric pressure. Therefore, the entire length of space inside the lumen of the atmospheric pressure tube 306 is at (or approximates) atmospheric pressure. Accordingly, the atmospheric pressure tube 306 provides an atmospheric reference to the IOP control system 200, which is possibly in a wet location that may be somewhat pressurized due to the presence of aqueous humor and possibly a bleb. While the atmospheric pressure tube 306 is shown with its opening disposed between the sclera of the eye and the patch 308, other embodiments have the atmospheric pressure tube terminating in the patient's own sclera through a small incision at any location around the globe of the eye.

Some embodiments include an external unit (e.g., handheld or wearable) used to support the IOP control system. For example, an external unit may provide charging or data collection capability. It also may include its own pressure sensor for determining atmospheric pressure. Information from the implanted IOP control system 200 may be broadcast or otherwise transmitted from the data transmission module 225 to the external unit, thereby enabling the external unit to verify the readings from the pressure sensor P3 indicative of pressure at the dry subconjunctiva under the patch 308. In the event that the atmospheric pressure reading taken at P3 is not a one-to-one match or does not otherwise correspond with the pressure taken via the external atmospheric reading with the external unit, correction algorithms may be employed to ensure an accurate pressure reading. Accordingly, the IOP control system may be calibrated to provide an accurate assessment of atmospheric pressure after implantation.

When used with an electronic valve or pump, an active drug delivery system, or a stand-alone IOP monitor, the IOP control system 200 permits continuous system operation without dependency on an external device (e.g. handheld or wearable) since IOP can be determined solely based on on-board (on implant) sensors.

In one example for treating an ocular condition, the IOP control system 200 is implanted in the subconjunctival pocket so that the plate 302 lies between the conjunctiva (or eye socket) and sclera, with the anterior device border disposed approximately 8-10 millimeters posterior of the limbus. The drainage tube 304 is arranged to extend in the anterior direction from the plate 302 and its open end is implanted into the anterior chamber of the eye. Aqueous humor may flow through the drainage tube 304 from the anterior chamber, relieving high IOP conditions. Accordingly, the drainage tube 304 may be filled with a moving liquid.

In the example shown, the atmospheric pressure tube 306 is arranged to also extend in the anterior direction from the plate 302. Because it may have a length less than the length of the drainage tube 304, the opening of the atmospheric pressure tube 306 ends at a position below the conjunctiva, between the conjunctiva and the sclera. In some examples, it may be held within the sclera. In use, it may become filled with stationary fluid, but will provide an atmospheric reference as detected by P3, associated with the lumen of the atmospheric pressure tube 306. In some examples, the lumen of the atmospheric pressure tube 306 may contain air instead of stationary fluid, or some combination of both. The pressure detected by the sensor P3 will still provide an indication of atmospheric pressure. However, over time the air may become replaced with stationary fluid, which also will reflect data indicative of atmospheric pressure.

With the drainage tube 304 implanted and the atmospheric pressure tube 306 arranged as desired, the surgeon can implant the patch 308 over the end of the atmospheric pressure tube 306. As described above, the patch 308 may be formed of donor sclera, pericardium, or other graft material. In the example shown, the patch 308 is disposed over both the opening in the atmospheric pressure tube 306 and over the drainage tube 304. Other embodiments include two patches, one over each tube. This may be particularly suitable when the drainage tube 304 and the atmospheric pressure tube 306 are not arranged side-by-side, as they are in the example shown. The patch 308 is sutured to the globe to both secure the tubes 304, 306, and protect the conjunctiva tissue from wear or trauma that may occur over time as the conjunctiva contacts and rubs on the exterior of the tubes or on the opening of the atmospheric pressure tube 306. As can be seen in FIG. 4, the sutures are disposed at the corners. As such, the patch is not sealed about the opening to the atmospheric pressure tube 306, and therefore is breathable about the edges. Accordingly, the patch 308 is loose enough and compliant enough that the opening in the atmospheric pressure tube 306, while under the patch 308, is still able to be pressurized at amounts indicative of external atmospheric pressure.

Once fully implanted, the IOP control system 200 may determine and regulate IOP using the pressure of the anterior chamber as detected by the sensor P1 and the representative atmospheric pressure taken at the atmospheric pressure tube 306 by the pressure sensor P3. The IOP control system 200 may also account for pressure measured by the sensor P2, whether at the drainage or bleb site.

Based upon the data obtained, the IOP control system 200 may regulate flow through the drainage tube 304 to maintain IOP within acceptable levels. Accordingly, the IOP control system 200 may be used to treat ocular conditions based on an IOP determined using pressure readings obtained through the atmospheric pressure tube opening at a dry location under the patch within the subconjunctival space.

In one aspect, as indicated above, the IOP control system is implanted into an eye for monitoring of IOP, but is not arranged to drain aqueous humor, and therefore does not compensate for pressure variances from a desired IOP. In yet other examples, the IOP control system is implanted in the eye in a first, non-draining state, but sometime after the implantation concludes, the IOP control system is changed to a second draining state. For example, a surgeon may implant the IOP control system in an eye in an implantation surgery, and use the IOP control system merely for monitoring. At some point in time later than the implantation surgery, the surgeon may determine that drainage from the anterior chamber would benefit the patient. At that time, the surgeon may activate a valve or otherwise change the state in the IOP control system to permit drainage to flow through the drainage tube to a drainage site. In one example, the surgeon may implant the IOP control system, but maintain the system in the first non-draining state until the eye has healed from the surgery. After healing, the system may be changed from a non-draining state to the second draining state to provide IOP control and pressure relief. Changing states may occur using a valve that may be electronically actuated at a desired time under the control of the processor, may occur using a bioerodable or biodegradable material that may permit flow only after a blocking material in the drainage tube sufficiently erodes, or using other methods. Other treatments methods are also contemplated.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

The invention claimed is:

1. An IOP (intraocular pressure) monitoring device for implantation in an eye of a patient, comprising:
   a drainage plate;
   a drainage tube having a first opening and a second opening, the drainage tube being configured to extend into an anterior chamber of the eye and extend to a first sensor outside the anterior chamber, the first sensor in fluid communication with the first opening of the drainage tube, wherein the first opening is located in the anterior chamber and the second opening is formed in the drainage plate so that aqueous humor can flow from the first opening in the anterior chamber to the second opening in the drainage plate;
   an atmospheric sensing subsystem coupled to the drainage tube, the atmospheric sensing subsystem configured to be exposed to a pressure representative of atmospheric pressure, the atmospheric sensing subsystem comprising:
   a second an atmospheric pressure sensor; and
   an atmospheric pressure tube having an opening spaced from the atmospheric pressure sensor and in fluid communication with the atmospheric pressure sensor;
   a patch, separate from the drainage plate, attachable to a globe of the eye and configured to lie over the opening of the atmospheric pressure tube such that the opening of the atmospheric pressure tube is exposed to the pressure representative of atmospheric pressure under the patch.

2. The IOP monitoring device of claim 1, wherein the drainage tube comprises walls having electrical leads configured to provide power and communication to and from the atmospheric sensing subsystem.

3. The IOP monitoring device of claim 1, wherein the patch comprises one of pericardium or donor sclera.

4. The IOP monitoring device of claim 1, wherein the patch is configured to overlie at least a portion of the drainage tube and secure the drainage tube in place in the eye.

5. The IOP monitoring device of claim 1, wherein the atmospheric pressure sensor is configured to detect pressure within the atmospheric pressure tube.

6. The IOP monitoring device of claim 1, wherein the first sensor is a pressure sensor disposed to measure pressure in the anterior chamber, and the atmospheric pressure sensor is a pressure sensor disposed to measure the pressure representative of atmospheric pressure, the IOP monitoring device being configured to compare the pressure in the anterior chamber to the pressure representative of atmospheric pressure.

7. The IOP monitoring device of claim 6, further comprising a processor configured to compare the pressure in the anterior chamber to the pressure representative of atmospheric pressure and determine an IOP.

8. The IOP monitoring device of claim 1, wherein the drainage tube is configured to convey aqueous humor from the anterior chamber to a drainage site outside the anterior chamber.

9. The IOP monitoring device of claim 8, wherein the device is part of an IOP control system for implantation in the eye of the patient to provide drainage from the anterior chamber of the eye to a drainage location at the eye, comprising:
   a second sensor configured to detect pressure at the drainage site;
   a valve system in fluid communication with the drainage tube and configured for implantation in the eye, the valve system being arranged to control drainage flow through the drainage tube between the anterior chamber and the drainage site; and
   a processor in communication with and configured to receive data from the first sensor, the atmospheric pressure sensor, and the second sensor, the processor being configured to control the valve system based on the received data to maintain desired pressures in the anterior chamber and at the drainage site.

10. The IOP monitoring device of claim 6, wherein the atmospheric pressure sensor is configured to measure the atmospheric pressure under the patch away from the drainage plate such that the atmospheric pressure sensor under the patch is not exposed to aqueous humor drainage from the drainage plate.

11. The IOP monitoring device of claim 9, further comprising a pump coupled to the valve system to increase movement of aqueous humor through the drainage tube.

12. The IOP monitoring device of claim 1, wherein the drainage tube and the atmospheric pressure tube are parallel.

13. The IOP monitoring device of claim 1, further comprising
   a second sensor configured to detect pressure at the drainage site; and
   a processor communicatively coupled to the first sensor, the atmospheric pressure sensor, and the second sensor.

* * * * *